(12) United States Patent
Berger et al.

(10) Patent No.: US 9,138,010 B2
(45) Date of Patent: Sep. 22, 2015

(54) FERMENT ACTIVATOR BASED ON LACTIC ACID BACTERIA, AND METHOD OF PREPARING A PRODUCT USING SAID ACTIVATOR

(75) Inventors: Claudette Berger, Mennecy (FR); Sonia Huppert, Vincennes (FR); Annie Mornet, Mondion (FR)

(73) Assignee: DuPont Nutrition Biosciences ApS, Copenhagen K (DK)

( * ) Notice: Subject to any disclaimer, the term of this patent is extended or adjusted under 35 U.S.C. 154(b) by 2201 days.

(21) Appl. No.: 10/569,852

(22) PCT Filed: Sep. 3, 2004

(86) PCT No.: PCT/FR2004/002254
§ 371 (c)(1),
(2), (4) Date: Feb. 27, 2006

(87) PCT Pub. No.: WO2005/024001
PCT Pub. Date: Mar. 17, 2005

(65) Prior Publication Data
US 2007/0010003 A1    Jan. 11, 2007

(30) Foreign Application Priority Data
Sep. 3, 2003  (FR) .................... 03 10423

(51) Int. Cl.
| A23C 9/123 | (2006.01) |
| C12N 1/38 | (2006.01) |
| C12N 1/20 | (2006.01) |

(52) U.S. Cl.
CPC ............. *A23C 9/1234* (2013.01); *A23C 9/1238* (2013.01); *C12N 1/20* (2013.01); *C12N 1/38* (2013.01)

(58) Field of Classification Search
CPC ........ C12N 1/20; C12N 1/38; C12N 15/1037; C12N 15/52; C12N 15/625; C12N 15/746; A23C 19/0323; A23C 19/0325; A23C 19/0682; A23C 9/123; A23C 9/1234; A23C 9/1238; A23V 2002/00; A23V 2200/08; A23V 2200/318; A23V 2200/3204; A23V 2250/5114; A61K 2300/00; A61K 35/74; A61K 45/06

See application file for complete search history.

(56) References Cited

U.S. PATENT DOCUMENTS

| 4,664,919 A | * | 5/1987 | Yan et al. ..................... 426/46 |
| 6,610,530 B2 | * | 8/2003 | Blank et al. ................ 435/252.9 |
| 6,863,918 B2 | * | 3/2005 | Bindels et al. ................ 426/590 |
| 6,953,574 B2 | * | 10/2005 | Sobol et al. ................. 424/93.45 |
| 7,291,355 B2 | * | 11/2007 | Zindel et al. .................... 426/34 |
| 2002/0034815 A1 | * | 3/2002 | Blank et al. ................ 435/252.3 |

FOREIGN PATENT DOCUMENTS

| DE | 1 201 748 A2 | 5/2002 |
| EP | 0 059 113 A2 | 9/1982 |
| FR | 2 814 469 A1 | 9/2000 |
| WO | 0224870 | * 3/2002 |

OTHER PUBLICATIONS

International Search Report received in International (FR) Application PCT/FR04/02254, dated Mar. 11, 2005.
*Lactobacillus acidophilus* Utilization of Sugars and Production of a Fermented Soybean Product, N. J. Stern et al., J. Inst. Can. Sci. Technol. Aliment., vol. 10, No. 3, Jul. 1977, pp. 197-200.
Database Biosis Online Biosciences Information Service, Philadelphia, PA: *Lactobacillus delbrueckii*subsp. bulgaricus and heat stress, Gousebet et al., Mededelingen Faculteit Landbouwkundige en Toegepaste Biologische Wetenschappen Universiteit Gent., vol. 64, No. 5a, 1999, pp. 259-265.

* cited by examiner

*Primary Examiner* — Debbie K Ware
(74) *Attorney, Agent, or Firm* — Marshall, Gerstein & Borun LLP

(57) ABSTRACT

The present invention relates to an activator for a lactic bacteria-based ferment, characterized in that it comprises at least:
  one reducing disaccharide,
  one non-reducing disaccharide,
  an alkaline metal salt and/or an alkaline earth metal salt.
The invention also relates to the ferment which is activated by means of said activator.
The present invention is also concerned with the process for preparing an industrial product or food product, characterized by the use of the activator.

23 Claims, No Drawings

FERMENT ACTIVATOR BASED ON LACTIC ACID BACTERIA, AND METHOD OF PREPARING A PRODUCT USING SAID ACTIVATOR

CROSS-REFERENCE TO RELATED APPLICATIONS

This application is the U.S. national stage application of PCT/FR04/02254, filed Sep. 3, 2004, which claims the benefit of French Patent Application 03 10423, filed Sep. 3, 2003.

The present invention relates to an activator for a lactic bacteria-based ferment, use of that activator for the preparation of industrial products or food products, and the process for preparing those products, characterised by use of the activator.

Lactic bacteria are used in a number of industries, particularly in the agri-food industry. They are used, amongst other things, to ferment, flavour, refine or texture foods, particularly milk products or "cooked meat" products. They are also used to protect the media in which they are incorporated from being contaminated by other micro-organisms, and they are also used for their probiotic action.

Depending on the use to which they are put, lactic bacteria are marketed in the form of compositions comprising mixtures of lactic bacteria, namely "ferments" or "starters". The most frequently used lactic bacteria which are present in ferments are those belonging to the species of *Lactococcus, Streptococcus, Lactobacillus, Leuconostoc, Pediococcus, Bifidobacterium, Brevibacterium, Camobacterium, Enterococcus, Micrococcus, Vagococcus, Staphylococcus, Bacillus, Kocuria, Arthrobacter* and *Corynebacterium*. These lactic bacteria are used alone or mixed.

Lactic bacteria which can also be cited are those of the thermophilic type, particularly *Streptococcus thermophilus, Lactobacillus casei, Lactobacillus paracasei, Lactobacillus helveticus, Lactobacillus delbrueckii* subsp. *Bulgaricus, Lactobacillus bulgaricus* and *Lactobacillus acidophilus*, but this list is not exhaustive.

These ferments are generally in the form of concentrates, either in dry, lyophilised or frozen form, or in the form of a suspension, and they are used most frequently in the form of a suspension. In the case of dry, lyophilised or frozen lactic bacteria, they need to be placed in suspension prior to use.

These concentrated formulation types have the two-fold advantage that they preserve the viability of the cultures over a long period of time, and are particularly suited to direct seeding wherein the ferment is introduced directly into the medium to be treated or to be seeded. An advantage of this latter case is that the ferment does not need to be placed in culture medium prior to use, unlike so-called semi-direct seeding.

Although the present invention can also be applied effectively to semi-direct seeding, it proves to be quite particularly worthwhile for so-called direct seeding for the following reason: when the bacteria are introduced into the medium to be treated or to be seeded, e.g. processed milk, during direct seeding i.e. in the form of a dry, liquid or frozen concentrate, the bacteria do not take effect straight away and require time to become active. The fact that this type of ferment needs time to become active means that time is an adaptation time lapse which corresponds firstly to re-establishment of the stored bacteria into its natural form (rehydration phase of the bacteria), and secondly to restoration of its metabolic activity.

Manufacturers have therefore perfected activators for being placed in contact with the ferments prior to direct or semi-direct seeding, in order to re-activate the ferments.

Now, with regard to the question of re-activating the lactic bacteria, the activators currently available are unsuitable because they do not enable the activity of the lactic bacteria to be preserved nor their texturing properties, particularly during periods of at least 24 hours of activation at ambient temperature.

In order to meet industrial requirements it has become necessary to find an activator for lactic bacteria with properties enabling the properties of the lactic bacteria to be preserved, particularly at ambient temperature.

Unexpectedly, the inventors have shown that by contacting a lactic bacteria-based ferment with an activator according to the invention prior to being introduced into the medium to be treated or seeded it was possible to preserve the stable activity of the bacteria.

The expression, "to preserve the stable activity of the bacteria" means that the bacteria preserve their acidification properties of the medium to be treated or seeded whilst they are being re-activated by the activator and are not yet seeded in said medium to be treated or seeded, with no, or with very little, multiplication of cells. The expression, "medium to be treated or to be seeded" means the medium into which the activated or non-activated ferment is introduced. It can, for example, be a milk-based medium, or a fruit juice-based medium, or a soya extract-based medium.

With this aim, the present invention proposes as its first object an activator for a lactic bacteria-based ferment, characterised in that it comprises at least:
  one reducing disaccharide,
  one non-reducing disaccharide,
  one alkaline metal salt and/or one alkaline earth metal salt.

Its second object is the use of that activator to activate a lactic bacteria-based ferment prior to or during direct seeding into a medium to be treated.

Another aspect of the present invention is concerned with a ferment based on lactic bacteria activated by way of the activator according to the invention.

Finally, the present invention has as its fourth object a process for preparing a product which contains at least one ferment, characterised by the use of the activator or ferment which has been activated according to the invention.

The direct seeding technique has determining advantages: immediate availability of the ferments with reduced bulk, possibility of producing complex mixes of different species or strains in specific and constant proportions, increased uniformity in terms of performance in comparison with traditional ferments which were prepared in the place of use, production taking place in specialised units during which each stage of the process is optimised and checked, strictly defined quality of the ferments.

The activator according to the invention is particularly worthwhile in terms of the ferment's stability upon direct seeding in liquid form.

Advantageously, the activator according to the invention permits re-activation of a ferment in an aqueous liquid, particularly in water.

As a result, the joint use of the activator with a lactic bacteria-based ferment advantageously makes it possible to preserve and standardise the metabolic activity of the activated bacteria over a relatively long period of time in comparison with that observed with the same foment in non-activated form.

Furthermore, quite advantageously, the use of the activator with a ferment makes it possible to delay cellular multiplication, or, quite simply, to restrict cellular multiplication, whilst allowing the ferments to resume their metabolic activity, the activated ferment according to the invention remaining effective.

The activator according to the invention is most particularly suited to ferments containing, inter alia, so-called thermophilic micro-organisms with an optimum growth temperature of between 35 and 45° C., but of up to between 30 and 50° C.

Finally, the activator according to the invention is advantageous in that it can be used in any industry, particularly the agri-food-, pharmaceutical-, cosmetic-, food-, agricultural industries, as well as within the domains of animal nutrition, animal food, and in hygiene in the broad sense, particularly body hygiene (e.g. toothpaste) or industrial hygiene.

Further advantageous and characteristics of the invention will emerge more clearly from reading the description of the examples hereinafter which have been given non-limitatively and purely by way of illustration.

The invention is concerned, first and foremostly, with an activator for a lactic bacteria-based ferment, characterised in that it comprises at least:
    a reducing disaccharide,
    a non reducing disaccharide,
    an alkaline metal salt and/or an alkaline earth metal salt.

The activator according to the invention contains at least one reducing disaccharide. Reducing disaccharides which are suitable according to the invention can be cited as lactose, lactulose, maltose, cellobiose or allolactose.

The reducing disaccharide can be added to the activator in the form of a pure compound or in the form of an impure mixture, as is the case, for example, with powdered milk or whey in cheese-making or casein-making, which contain at least one reducing disaccharide.

The activator according to the invention also contains at least one non-reducing disaccharide.

The non-reducing disaccharides which are suitable according to the invention can be cited as saccharose, threalose, or raffinose.

The activator according to the invention also contains at least one alkaline metal salt and/or an alkaline earth metal salt. Preferably, it is a sodium-, potassium-, calcium- or magnesium salt, such as for example sodium-, calcium-, magnesium- or potassium chloride, sodium- or potassium phosphate, sodium- or potassium orthophosphate, sodium- or potassium citrate, or sodium or potassium formiate.

The relative proportions of each constituent contained in the activator are as follows:
    30 to 50% of reducing disaccharides,
    30 to 50% of non-reducing disaccharides,
    10 to 30% of alkaline metal salts and/or an alkaline earth metal salts, the percentages being expressed by weight.

A ferment which is activated with the activator according to the invention is advantageously effective for a period of time of up to 72 hours, more particularly for a period of time of up to 48 hours, preferably for a period of time of up to 24 hours.

Thus, a ferment based on activated bacteria according to the invention is effective for a period of time of up to 72 hours, whereas the same ferment which has been rehydrated in water and non-activated shows a significant loss of activity after three hours.

Furthermore, the inventors have noted that the presence of the activator was advantageous in terms of the equilibrium of microbic populations of the activated system.

A particularly significant gain in productivity can be obtained for thermophilic bacteria-based ferments.

As can be seen from the examples given hereinafter, a lactic bacteria-based ferment which is activated according to the invention prior to being introduced into the medium to be treated restores an acidifying property much more quickly into the medium to be treated in comparison with the standard ferment, i.e. in non-activated form.

According to one variant of the invention, nutrients needed for maintaining the metabolic activity of the lactic bacteria are also associated with the activator according to the invention.

These nutrients generally include vitamins, yeast extracts, amino acids, peptides or proteins.

Similarly, co-factors useful for activating glycolysis can be present in the activator according to the invention. By way of example of these co-factors, the following mineral salts can be cited: $Ca^{2+}$, $K^+$, $Mg^{2+}$, $Mn^{2+}$, $Cu^{2+}$ and $Zn^{2+}$. They are generally used at a rate of between 0.1 and 2% by weight.

It is also possible to envisage incorporating texturing agents into the activator, e.g. polysaccharides or hydrocolloids, particularly carrageenans or xanthan gum, guar gum, carob bean gum, tara gum.

The activator according to the invention can be obtained simply by mixing its constituents, and is generally in dry, usually powdery, form. However, it is also possible to envisage formulating it in a lyophilised or frozen form.

The activator according to the invention can also be in liquid form.

According to one preferred variant of the invention, the activator according to the invention is in sterilised form and when used that sterile property is respected.

The second object of the present invention is the use of an activator according to the present invention for activating a lactic bacteria-based ferment prior to or during direct seeding in a medium to be treated or to be seeded.

Preferably, said activator is placed in contact with the lactic bacteria-based ferment in liquid medium, particularly water.

The use of this activator to activate, in liquid medium, a lactic bacteria-based ferment makes seeding possible in a continuous or discontinuous line, and the seeding can be automated and aseptic.

The invention also relates to an activated lactic bacteria-based ferment, characterised in that it associates with the lactic bacteria an activator according to the invention.

In the present example, the quantity used of the activator according to the invention is such that the constituents thereof are present in sufficient quantities to reveal significant activation of the lactic bacteria-based ferment.

The mass of ferment:mass of activator ratio is between 0.1 and 0.7, preferably between 0.2 and 0.6.

The activated lactic bacteria-based ferment according to the invention can be prepared in such a way that the lactic bacteria and the activator are associated within a liquid medium, particularly water.

The activator can be mixed with the ferment either prior to, or at the time of, use. However, according to one preferential embodiment, the ferment is used prior to its rehydration in the presence of an activator according to the present invention. Generally, this association takes place in a liquid medium, preferably water.

The activator is rehydrated in such a way that the quantity of activator is between 5% and 20% by weight of aqueous suspension, preferably between 7% and 15%.

Consecutive rehydration and activation of the ferment can be conducted at ambient temperature, particularly at a temperature of between 15° C. and 25° C., preferably of between 18° C. and 23° C., and, more particularly, under agitation conditions in order to optimise activation and homogenisation over time. The activated ferment is then used as such for the seeding, preferably direct seeding, of a medium to be treated.

The lactic bacteria which can be associated with an activator according to the invention include all the lactic bacteria usually used in industry, particularly in the agri-food-, pharmaceutical-, cosmetic-, food-, agricultural industries, as well as within the domains of animal nutrition, animal foods, and hygiene in the broad sense, particularly body hygiene (e.g. toothpaste) or industrial hygiene.

The activator according to the invention is also suitable for thermophilic lactic bacteria.

By way of example of lactic bacteria, the following bacteria belonging can be cited belonging to the species of *Streptococcus, Lactococcus, Lactobacillus, Leuconostoc, Bifidobacterium* and *Pediococcus*, and, in particular, *Lactococcus lactis, Lactococcus lactis* subsp. *diacetylactis, Lactococcus cremoris, Leuconostoc mesenteroides*.

Thermophilic lactic bacteria such as the following can also be considered: bacteria used within the dairy domain belonging to the species of *Propionibacterium, Brevibacterium* and *Bifidobacterium*, e.g. *Bifidobacterium lactis, Bifidobacterium bifidum, Bifidobacterium longum, Bifidobacterium infantis* or *Bifidobacterium adolescentis*.

A fourth object of the present invention is a process for the preparation of a product containing at least one ferment, comprising the following steps:
  (i) contacting a ferment comprising at least some lactic bacteria with an activator according to the present invention, in order to obtain a ferment in an activated form,
  (ii) seeding the medium to be treated with said ferment in an activated form.

With regard to the preliminary step (i), namely contacting the ferment with the activator claimed, it is generally carried out over a period of time sufficient to obtain the activated form and within a liquid medium, particularly water. The corresponding suspension can be obtained by adding a liquid, preferably an aqueous medium, to the mixture of the two constituents (activator and ferment) or by dispersing the two constituents consecutively in said liquid.

The process according to the invention can further comprise a step (iii) of incubating said medium to be treated under conditions favourable to the metabolic activity of the lactic bacteria in order to obtain a fermented product.

The process according to the invention can be carried out by the use of a seeding device.

The preferred seeding device for putting into practice the process according to the invention can be in the form of a sealed tank.

The seeding device for putting into practice the process according to the invention can also be in the form of a disposable tank and/or a tank which is secured to a movable station.

The sealed tank can be in the form of a pocket equipped with an internal agitation system and intake and outlet means.

One of the intake means makes it possible for the aqueous medium to reach the sealed tank for execution of step (i). The aqueous medium is sterilised beforehand, and is preferably filtered over a diaphragm of at most 0.45 µm, more particularly of at most 0.22 µm. It should be noted that tap water can be used.

One of the other intake means makes it possible for gas to reach the sealed tank. The gas intake will make it possible for the internal agitation system of the tank to be used.

In one particular instance of the invention, the internal agitation system can be constituted by a permeable internal pocket. In this case, the coaled tank comprises a permeable internal pocket and an external closed pocket. Agitation takes place by the successive injection of gas into the permeable internal pocket which allows the suspension to be transferred from the permeable internal pocket to the external closed pocket.

In another case, the agitation system is constituted by a U-shaped sealed tank. In this case, agitation takes place by the successive injection of gas into a U-shaped arm which allows the suspension to be transferred from one side to the other of the U-shape.

Advantageously, a gas is used which can be air or a gas which does not affect the breathing and/or oxidation of the microorganisms, ferments and bacteria, or a gas which is chemically and biologically inert, e.g. argon, nitrogen or carbon dioxide, or mixtures thereof.

The term, "biologically inert" means a gas which does not interfere with microorganism multiplication and degradation.

The pressure of the gas inside the sealed tank, during agitation, is less than 5 bars, preferably less than 1 bar.

Gas can also be injected at regular time intervals. Preferably, the gas is injected under pressure at time intervals of between 0.5 minutes and 60 minutes.

Agitation makes it possible for the ferments and activator to be placed in suspension in the aqueous medium.

After agitation, the suspension of ferments and of activator is kept in suspension by injecting gas in accordance with the same successive gas injection principle.

The sealed tank is emptied aseptically through the outlet means, thereby enabling step (ii) of the process to be carried out.

The emptying is carried out by injecting gas inside the sealed tank, or by transferring the aqueous suspension of ferments and activator by means of a pump or by means of gravity.

Seeding of the medium to be treated with said ferment in an activated form (step (ii)) is carried out at a flow rate of between 10 ml/min and 1000 ml/min, preferably of between 100 ml/min and 500 ml/min.

Step (ii) according to the invention is carried out at a temperature of between 5° C. and 45° C.

Step (ii) according to the invention is carried out over a period of time of up to 72 hours, more particularly over a period of time of up to 48 hours, preferably over a period of time of up to 24 hours.

Step (ii) can be carried out in accordance with a number of variants.

A first variant of step (ii) of the process consists in seeding the medium to be treated one single time with said ferment in activated form. This is effected by emptying the tank(s) one single time. This seeding is batch seeding (one single tank) or multi-batch seeding (several tanks).

A second variant of step (ii) of the process consists in seeding the medium to be treated continuously with said ferment in activated form.

A third variant of step (ii) of the process consists in seeding the medium to be treated discontinuously with said ferment in activated foam.

The term "discontinuous" means a seeding cycle which is carried out in the following way: the medium to be treated is seeded during a time lapse, seeding is then stopped, and is then recommenced, this going on for a number of cycles.

Within the framework of this third variant, seeding of the medium to be treated with said ferment in activated form (step (ii)) is carried out at a rate of between 10 ml/min and 1000 ml/min, preferably of between 100 ml/min and 500 ml/min, at regular or irregular time intervals of between 1 minute and 600 minutes.

It should be noted that the sealed tank is advantageously secured to a movable station which can be moved anywhere along the industrial chain before or after step (i) of the process according to the invention.

The preferred type of tank for implementing the process according to the invention is of the disposable type and/or is sterile.

The tank is preferably made of a flexible material, eg. polypropylene, polyester, polyamide, cellulose, or any other flexible material compatible with food products, and is preferably polyethylene.

The advantage of using the process according to the invention with the seeding device as described hereinabove is that direct seeding takes place in liquid form kept at ambient temperature, is sterile, is standardised, and can be adapted to any type of production and guarantees bacteriological quality.

Another advantage of using the process according to the invention with the seeding device such as described hereinabove is that the step of seeding the lactic ferment is simplified and made reliable The present invention also extends to the various ways of storing the activator claimed.

In fact, the activator according to the invention can be formulated in a separate packaging from that of the lactic bacteria-based ferment with which it is intended to be associated, or, conversely, it is possible to envisage one common packaging within which the activator according to the invention and the lactic bacteria-based ferment are both present, separately or otherwise.

This second packaging variant can also be designed in such a way that it is suitable for prior mixing of the ferment and activator, and thus for preparing the so-called activated ferment prior to seeding a medium to be treated.

The following examples are given non-limitatively and by way of illustration of the present invention.

EXAMPLES

Methods

Lactic bacterial, alone or mixed, behave in a great variety of ways. In the case of the present invention, the acidifying activity has been kept as a criterium for characterising the activity of the bacteria.

A milky medium was acidified in the following chronological order:
inoculation of a milk (pH close to 6.6),
increase of lactic bacterial population by hydrolysis of the milk lactose,
production of lactic acid by the lactic bacteria, which is translated by a reduction in the pH of the milky medium,
stoppage in growth of the lactic bacteria which are gradually inhibited by the lactic acid which has formed,
undertaking production of acid until a pH of 4.5 is reached.

The acidifying activity has been assessed in the following examples with the aid of an automatic system for following and characterising the lactic ferments by measuring the pH in real time, also called CINAC hereinafter.

The CINAC is composed of:
electrodes combined with Ingold type glass (24 gauges for measuring the pH placed in conical flasks containing the seeded medium and 8 temperature measuring gauges)
a water bath controlled by a thermostat and in which the conical flasks are placed
an electronic card supplying an analog signal and an electronic interface converting this latter into digital form
a PC micro-computer equipped with CI AC software for carrying out the following functions:
configuration of system
acquisition, processing and storing of data
calibration of sensors to pH7 and pH4
calculation of kinetic descriptors
graphic display of processed data
conversion of data for use of this latter on other software
programming of thermal cycles in order to regulate the temperature of the water bath
compensation of temperatures in order to correct variations of temperature over pH
(this correction is made thanks to a proportional-integral-derivative (PM) controller
execution of procedures for testing the calibration data for the purpose of detecting any dysfunctions associated with the probes.

The CINAC processes the data by supplying curves for the acidification kinetics and descriptors of these latter.

The curves which describe the kinetics represent the trends of the pH and of the rate of acidification (dpH/dt), as a function of time. They witness various stages of growth: re-adaptation phase, acceleration, exponential phase, deceleration, stationary phase.

The descriptors which have been kept in the examples for the purpose of characterising the acidification kinetics are as follows:
Ta=latent period in mins (time alter which the pH has varied by 0.08 upH below its initial value)
Vm=maximum rate of acidification in upH/mins {rate taken at the maximum absolute value of the derivative dpH/dt=f(t))
5.20 time=time to obtain a pH of 5.20 in minutes
4.75 time=time to obtain a pH of 4.75 in minutes.

On the basis of all these parameters it is possible to distinguish either a gain or loss of productivity.

The lactic bacteria present in the rehydration medium was counted with the passage of time in accordance with the following method:

The ferment was rehydrated and activated by means of activator (composition A or B hereinafter), as indicated under 1-3. The activated ferment thus obtained is stored for 24 hours. After being stored, the bacterial population is measured after different times of storage. The population is measured after different times which can range from 1 hour (T1 h) to 72 hours (T72 h) of storage.

The dilutions are effected in a tryptone salt prepared in accordance with the following protocol: 1 g tryptone, 8.5 g NaCl are placed in 1 liter of water. The solution obtained is distributed in a tube of 9 ml capacity and is then treated for 15 minutes at 120° C.

The dilutions effected from these tubes are as follows: $10^{E-6}$; $10^{E-7}$; $10^{E-8}$; $10^{E-9}$; $10^{E-10}$.

1 ml of those dilutions is then drawn off and placed in Pétri dishes. Various geloses are then poured onto the dishes, and they are incubated in accordance with the following protocol:

| Bacteria under investigation | Medium used | Inoculation and Incubation |
| --- | --- | --- |
| Streptoccocus thermophilus | M17 Merck ready for use | Mass inoculation 37° C. - 48 h anaerobiosis (CO2) |
| Lactobacillus delbrueckii bulgaricus | MRS MERCK ready for use acidified to pH 5.4 | Mass inoculation 37° C. - 48 h anaerobiosis (CO2) |

-continued

| Bacteria under investigation | Medium used | Inoculation and Incubation |
|---|---|---|
| L acidophilus (associated with other bacteria) | MRS + clindamycine at a rate of 0.1 mg/l | Mass inoculation 37° - 48 h anaerobiosis (CO2) |
| Bifidobacterium | MRS + dicloxacilline | Mass inoculation 42° C. - 48 h anaerobiosis (CO2) |
| Lactobacillus paracasei paracasei | MRS MERCK ready for use | Mass inoculation 37° - 48 h anaerobiosis (CO2) |
| Lactobacillus acidophilus (used alone) | MRS MERCK ready for use | Mass inoculation 37° - 48 h anaerobiosis (CO2) |

EXAMPLE 1

Preparation of Co-Enzymes According to the Invention 1-1/Preparation of a Co-Enzyme (Composition A):

The activator according to the invention is prepared in a 1 liter sterile flask containing a double-ringed bar magnet of 45 mm. The various components of the mixture are given in Table I hereinafter:

TABLE 1

Composition A

| Products | Quantity (g) |
|---|---|
| Skimmed milk powder | 65 |
| Saccharose | 24.5 |
| MgSO4 | 1.6 |
| MgCO3 | 0.8 |
| CaCO3 | 0.8 |
| Yeast extract | 4.1 |
| MnSO4 | 1.6 |
| Ammoniacal iron-citrate | 1.6 |

1.2/Preparation of a Co-Enzyme (Composition B):

The activator according to the invention is prepared in a 1 liter sterile flask containing a double-ringed bar magnet of 45 mm. The various components of that mixture are given in Table II hereinafter:

TABLE II

Composition B

| Products | Quantity (g) |
|---|---|
| Lactose | 42 |
| Saccharose | 42 |
| Sodium formiate | 16 |

1-3/Preparation of a Concentrated Ferment Which has been Rehydrated According to the Invention In the following examples, the activator described under 1-1 or 1-2 is then mixed with 50 g lyophilised ferment and 870 g sterile water. The dry mixture is poured into the water with magnetic agitation, and is dissolved in a few minutes. In this way, 1 liter is obtained of a solution containing 50 g lyophilised ferment.

The resulting rehydration temperature of the mixture, namely ferment and activator, is conducted in accordance with the so-called "winter" thermal cycle. That cycle restores the temperature rise for an amount of 251, starting at 15° C. and attaining a temperature of 20° C. which is reached over about 20 hours.

EXAMPLE 2

Measuring the Acidifying Activity of Various Ferments 2-1/Streptococcus thermophilus Strains The strain tested is a thermophilic strain. To be more exact, it is one of the strains of Streptococcus thermophilus which is a lactic ferment marketed by RHODIA FOOD S.A.S.

The Streptococcus thermophilus strain is rehydrated and activated by means of the activator (composition A), as stated under 1-3. The activated strain which is thus obtained is stored for 24 hours at the temperature stated under 1-3. After storage, the activity of the bacterial concentrate is measured after various storage times by means of the CINAC, as indicated hereinabove. The activity is measured after 20 minutes (regarded as time T0), after 1 hour (T1 h), after 3 hours ((T3 h), after 6 hours (T6 h), after 12 hours (T12 h), after 16 hours (T16 h) and after 24 hours (T24 h) of storage.

The rehydrated strain which has been activated is drawn off after different storage times, and is seeded in half-fat milk at 38° C. Owing to the concentration of bacteria, dilution is undertaken in order to be able to seed the acidification tests (1 g activated strain is dissolved in 200 ml milk which is used to measure the activity). The seeding has to be carried out immediately so as not to have an adverse effect upon the activity of the bacterial concentrate.

A reference activity is launched for each test carried out and employs 1 g lyophilised strain in 200 ml milk. The references are seedings made directly in the processed milk with the strain which has not been activated by the activator,
Measuring the Acidifying Activity Over Time:

The results obtained with this strain are shown in Table III hereinafter. The data in the tables takes into account increases obtained in terms of stability with the ferments activated according to the invention in comparison with their respective non-activated forms.

TABLE III

| Streptococcus thermophilus | Ta in mins | Max. rate in upH/mins | 5.20 time | Population of rehydrated ferment (in unit forming colony (ufc) |
|---|---|---|---|---|
| Reference rehydrated at 20° C. | 116 | 0.0157 | 252 | — |
| T0 | 105 | −0.0205 | 210 | — |
| T1 h | 109 | −0.0215 | 210 | 6 $10.^9$ |
| T3 h | 107 | −0.0213 | 210 | |
| T6 h | 110 | −0.0215 | 214 | 7 $10.^9$ |
| I12 h | 109 | −0.0216 | 216 | 6 $10.^9$ |
| T16 h | 107 | −0.0211 | 213 | 7 $10.^9$ |
| T24 h | I14 | −0.0216 | 221 | 6 $10.^9$ |

These results show that the latent period (Ta) varies very little, irrespective of the storage time of the activated strain. Furthermore, after 24 hours of storage, it is noted that the Streptococcus thermophilus strain has a 5.20 time of 221 minutes, which is virtually identical to the 5.20 time for test T0 (210 minutes). This means that its acidifying activity is not adversely affected after 24 hours of storage. An increase in acidifying activity of 42 minutes is noted between the 5.20 time of the rehydrated reference (252 minutes) and the T0 test (210 minutes).

From these results it becomes apparent that the activator behaves favourably towards the bacterial population present in the ferment, and, in particular, that the bacterial population is stable during storage.

2-2/Ferment Composed of *Streptococcus thermophilus* and *Lactobacillus delbrueckii bulgaricus*

The ferment tested comprises 2 strains of lactic bacteria, namely *Streptococcus thermophilus* and *Lactobacillus delbrueckii bulgaricus*. This is a ferment which is marketed by RHODIA FOOD S.A.S.

The tested ferment was rehydrated and activated by means of the activator of composition A, in accordance with the method stated under 1-3. The activated ferment thus obtained is stored for 24 hours at the temperature stated under 1-3. During that storage period, the activity of the bacterial concentrate is measured after various storage times by means of the CINAC, as indicated hereinabove. The activity is measured after 1 hour (T1 h), after 4 hours (T4 h) and after 24 hours (T24 h) of storage.

The rehydrated strains which have been activated are drawn off after different times of storage, and are seeded in half-fat milk at 43° C. Owing to the concentration of bacteria, dilution is carried out so as to be able to seed the acidification tests (1 g activated strain is dissolved in 200 ml milk which is used to measure the activity). The seeding has to be carried out immediately so as not to adversely affect the activity of the bacterial concentrate.

A reference activity is launched for each test carried out, using 1 g lyophilised strain in 200 ml milk. The references are seeded directly in the processed milk with strain which has not been activated by the activator.

Measuring the Acidifying Activity Over Time:

The results obtained with each of the strains are shown in Table IV hereinafter. The data given in the tables takes into account increases obtained in terms of stability and productivity with ferments which have been activated according to the invention in comparison with their respective non-activated forms.

TABLE IV (Composition A)

| Ferment for yoghurt | Ta in mins | Max. rate in upH/min | 4.75 time | Total population of rehydrated ferment (in unit forming colony (ufc)) |
|---|---|---|---|---|
| Reference rehydrated at 20° C. | 85 | −0.019 | 290 | — |
| T1 h | 75 | −0.019 | 250 | $2.10^{E}10$ |
| T4 h | 75 | −0.019 | 250 | $2.10^{E}10$ |
| T24 h | 85 | −0 019 | 265 | $2.10^{E}10$ |

The results show an increase in activity of 40 minutes for the 4.75 time between the rehydrated reference (290 minutes) and the T1 h activated ferment (250 minutes). An increase in activity is observed up until 24 hours of storage: the 4.75 time is shorter. The total population and acidifying activity is stable for 24 hours at the temperature stated hereinabove under 1-3.

2-3/Ferment Composed of 4 Strains

The ferment tested comprises 4 strains of lactic bacteria, namely *Streptococcus thermophilus, Lactobacillus delbrueckii bulgaricus, Lactobacillus acidophilus* and *bifidobacterium lactis*. The ferment is one marketed by RHODIA FOOD S.A.S.

The ferment was rehydrated and activated by means of the activator (composition B), as indicated under 1-3. The activated ferment thus obtained is stored for 24 hours at the temperature indicated under 1-3. During that storage time, the activity of the bacterial concentrate is measured after different storage times by means of the CINAC, as indicated hereinabove. The activity is measured after I hour (T1 h), after 2 hours (T2 h), after 4 hours (T4 h), after 8 hours (T8 h), after 12 hours (T12 h) and after 24 hours (T24 h) of storage.

The rehydrated strains which have been activated are drawn off after different storage times, and are seeded in half-fat milk at 43° C. Owing to the concentration of bacteria, dilution is effected in order to be able to seed the acidification tests (1 g activated strain is dissolved in 200 ml milk which is used to measure the activity). The seeding has to be carried out immediately so as not to adversely affect the activity of the bacterial concentrate.

A reference activity is launched for each test carried out, using 1 g lyophilised strain in 200 ml milk. The references are seeded directly into the processed milk with the strain which has not been activated by the activator.

Measuring the Acidifying Activity Over Time:

The results obtained with each ferment are given in Table V hereinafter. The data given in the table takes into account increases obtained over time in respect of stability and productivity with ferments which have been activated according to the invention in comparison with their respective non-activated forms.

TABLE V (Composition B)

| Ferment for fermented milks | Ta (mins) | Max. rate (upH/mins) | 4.75 Time | Population of rehydrated ferment (in unit forming colony (ufc)) | | |
|---|---|---|---|---|---|---|
| | | | | *S. thermophilus/ L. bulgaricus* | *L. acidophilus* | *Bifidobacterius* |
| Reference rehydrated at 20° C. | 78 | −0.018 | 300 | — | — | — |

TABLE V-continued (Composition B)

| Ferment for fermented milks | Ta (mins) | Max. rate (upH/mins) | 4.75 Time | Population of rehydrated ferment (in unit forming colony (ufc)) | | |
|---|---|---|---|---|---|---|
| | | | | S. thermophilus/ L. bulgaricus | L. acidophilus | Bifidobacterius |
| T1 h | 82 | −0.019 | 275 | $5.10^{E}9$ | $3.10^{E}8$ | $2.10^{E}8$ |
| T2 h | 81 | −0.016 | 290 | $6.10^{E}9$ | — | — |
| T4 h | 77 | −0.016 | 290 | $5.10^{E}9$ | — | — |
| T8 h | 80 | −0.016 | 290 | $6.10^{E}9$ | $3.10^{E}8$ | $2.10^{E}8$ |
| T12 h | 78 | −0.017 | 290 | $5.10^{E}9$ | $3.10^{E}8$ | $2.10^{E}8$ |
| T24 h | 78 | −0.016 | 290 | $6.10^{E}9$ | $3.10^{E}8$ | $2.10^{E}8$ |

The results show an increase in activity of 25 minutes for the 4.75 time between the rehydrated reference (300 minutes) and the T1 h activated ferment (275 minutes). An increase in activity is observed up until 24 hours of storage: the 4.75 time is shorter. The total population and acidifying activity is stable over 24 hours at the temperature stated under 1-3.

EXAMPLE 3

3-1/Preparation of a Fermented Milk (Yoghurt)

Fermented milk (yoghurt) is prepared using activated ferments which have been prepared in accordance with Example 2-2. The viscosity of the fermented milk thus obtained is then measured.

Preparation of fermented milk (yoghurt): The fermentation support is obtained by adding to 100 ml of half-fat UHT milk (Petit Vendéen) 3% (weight/volume) of fat-free milk powder (Eurial). Sterility of the solution is obtained by means of pasteurisation for 10 minutes at 90° C. (internally). The fermentation support which is thus obtained is inoculated with the strain or ferment to be tested at a rate of 4 units per 100 liters, then incubated at 43° C. (in the water bath) until a pH of 4.6 is obtained. The pH is followed continuously by using a CINAC (1sbaert). The yoghurt which is obtained in this way is placed in a cabinet which is ventilated at 6° C., until it is analysed.

Rheological analyses on the yoghurt: only the viscosity is measured. The viscosity measurements are taken on the fermented milk after 1 and/or 7 and/or 14 days' storage, and its temperature is maintained at 6° C. The apparatus used is a RVF type Brookfield viscometer (Brookfield Engineering Laboratories Inc.) mounted on a Helipath stand (Brookfield Engineering Laboratories Inc.). The viscometer is equipped with a type C needle, and the oscillation speed applied to the needle is 10 revs/min.

3-2/Results of the pH and of the Viscosity on the Yoghurt Made With a *Streptococcus thermophilus* Ferment and With a *Lactobacillus delbrueckii bulgaricus* Ferment:

The ferment tested is identical to that used under 2-2, and comprises 2 strains of lactic bacteria, namely *Streptococcus thermophilus* and *Lactobacillus delbrueckii bulgaricus*.

The ferment tested has been rehydrated and activated using either the activator of composition A or the activator of composition B, in accordance with the method indicated under 1-3. The activated ferment thus obtained is stored for 24 hours at the temperature stated under 1-3. During storage, fermented milk is produced after different storage times (1 hour and 24 hours), and the viscosity and pH are measured in the way stated hereinabove under 3-1.

Measuring the Viscosity and pH Over Time in Accordance With the Method Described Under 3-1:

The results obtained with the ferment are given in Table VI hereinafter. The data given in that table takes into account the stability and productivity of the ferments which have been activated according to the invention in comparison with their respective non-activated forms.

TABLE VI

| | | Follow-up examples | | | |
|---|---|---|---|---|---|
| | | J + 1 | | 7 + 7 | |
| Name of Medium | | Viscosity in cps | pH | Viscosity in cps | pH |
| Activator of composition | T1 h | 51 200 | 4.57 | 50 800 | 4.49 |
| | T24 h | 50 900 | 4.55 | 49 700 | 4.50 |
| Reference | T1 h | 49 900 | 4.58 | 49 000 | 4.46 |
| | T24 h | 50 100 | 4.52 | 50 100 | 4.43 |

There are no significant differences between the yoghurt made with the reference and that made with the activated ferment, either in respect of pH or in respect of viscosity.

3.3/Results of pH and of Viscosity on the Yoghurt Made With a Ferment Composed of 4 Strains:

The ferment tested is identical to that used under 2-3, and comprises 4 strains of lactic bacteria, namely *Streptococcus thermophilus, Lactobacillus delbrueckii bulgaricus, Lactobacillus acidophilus* and *bifidobacterium lactis*.

The ferment tested has been rehydrated and activated by means of the activator of composition B, in accordance with the method indicated in 1-3. The activated ferment thus obtained is stored for 24 hours at the temperature stated under 1-3. During storage, fermented milk is produced after different storage times (1 hour, 4 hours, 8 hours and 12 hours), and the viscosity and pH are measured in the way stated hereinabove under 3-1.

Measuring the Viscosity and pH Over Time in Accordance With the Method Described Under 3-3:

The results obtained with the ferment are given in Table VII hereinafter. The data given in the table takes into account the stability and productivity of ferments activated in accordance with the invention in comparison with their respective non-activated forms.

| | J + 1 | | J + 14 | |
|---|---|---|---|---|
| Time in hours | Viscosity in cps | pH | Viscosity in cps | pH |
| 1 | 33 900 | 4.75 | 39 500 | 4.38 |
| 4 | 33 650 | 4.75 | 39 050 | 4.39 |
| 8 | 35 100 | 4.64 | 39 000 | 4.34 |

-continued

|  | J + 1 | | J + 14 | |
| --- | --- | --- | --- | --- |
| Time in hours | Viscosity in cps | pH | Viscosity in cps | pH |
| 12 | 32 400 | 4.70 | 39 500 | 4.44 |
| Reference | 33 000 | 4.74 | 39 500 | 4.40 |

The "yoghurt" or fermented milk made from the rehydrated ferment has similar properties to the reference following storage for 12 h at the temperature stated under 1-3.

EXAMPLE 4

Counting of 2 Probiotic Strains 4-1/Probiotic Strains

The tested strains are probiotic strains. To be more exact, they are strains of *Lactobacillus paracasei* (LC) and *Lactobacillus acidophilus* (LA) which are lactic ferments marketed by RHODIA FOOD S.A.S.

The LC and LA strains are rehydrated and activated by means of the activator (composition B), at a rate of $4.8\ 10^{E}9$ ufc per ml of rehydration medium. The solutions containing the rehydration medium and each of the strains are distributed into flasks of 125 ml capacity. They are placed in a room whose temperature is controlled at 18° C., and are agitated at 150 revs/min for 72 hours. During that storage, the population of bacteria is determined after different storage times. The counting is carried out after 20 minutes (regarded as time T0), after 1 hour (T1 h), after 5 hours (T5 h), after 24 hours (T24 h), after 48 hours (T48 h), and after 72 hours (T72 h) of storage.

The results obtained with each ferment are given in Table VIII hereinafter.

TABLE VIII

| | Counts | | | | | |
| --- | --- | --- | --- | --- | --- | --- |
| Strains | T0 | T1 h | T5 h | T24 h | T48 h | T72 h |
| LC | $4.8\ 10^{E}9$ | $5.8\ 10^{E}9$ | $4.6\ 10^{E}9$ | $5.5\ 10^{E}9$ | $4.2\ 10^{E}9$ | $4.8\ 10^{E}9$ |
| LA | $4.8\ 10^{E}9$ | $4.7\ 10^{E}9$ | $3.9\ 10^{E}9$ | $4.2\ 10^{E}9$ | $4.6\ 10^{E}9$ | $3.9\ 10^{E}9$ |

These two probiotic strains which were rehydrated and activated in accordance with the invention have very good stability during 72 hours of storage at the temperature stated under 1-3.

The invention claimed is:

1. An activator for re-activating a lactic acid bacteria-based ferment in a form of a concentrate, comprising at least:
   30 to 50% by weight of reducing disaccharides,
   30 to 50% by weight of non-reducing disaccharides,
   10 to 30% by weight of alkaline metal salts and/or an alkaline earth metal salt, wherein all percentages are expressed by weight of the total dried weight of the activator.

2. An activator according to claim 1, wherein the lactic acid bacteria are thermophilic lactic acid bacteria.

3. An activator according to claim 1, wherein the reducing disaccharide is lactose, lactulose, maltose, cellobiose or allolactose.

4. An activator according to claim 1, wherein the non-reducing disaccharide is saccharose, threalose or raffinose.

5. An activator according to claim 1, wherein the alkaline metal salt and/or the alkaline earth metal salt is a sodium-, potassium-, calcium- or magnesium salt.

6. An activator according to claim 1, further comprising nutrients for maintaining a metabolic activity of the lactic acid bacteria.

7. An activator according to claim 1, in combination with an activated lactic acid bacteria-based ferment.

8. An activator according to claim 5, wherein the alkaline metal salt and/or the alkaline earth metal salt is sodium-, calcium-, magnesium- or potassium chloride, sodium- or potassium phosphate, sodium- or potassium orthophosphate, sodium- or potassium citrate, or sodium or potassium formiate.

9. An activator according to claim 1 which is in liquid form.

10. A method for activating a lactic acid bacteria-based ferment before or during direct seeding in a medium to be treated or seeded comprising contacting said ferment with an activator comprising at least:
    30 to 50% by weight of reducing disaccharides,
    30 to 50% by weight of non-reducing disaccharides,
    10 to 30% by weight of alkaline metal salts and/or an alkaline earth metal salt, wherein all percentages are expressed by weight of the total dried weight of the activator.

11. The method according to claim 10, wherein the contacting is conducted in a liquid medium.

12. A method according to claim 11, wherein the liquid medium is water.

13. A process for the preparation of a product containing at least one ferment, comprising the following steps:
    (i) contacting a ferment comprising at least some lactic acid bacteria with an activator in a form of a concentrate comprising:
    30 to 50% by weight of reducing disaccharides,
    30 to 50% by weight of non-reducing disaccharides,
    10 to 30% by weight of alkaline metal salts and/or an alkaline earth metal salt,
    wherein all percentages are expressed by weight of the total dried weight of the activator; and
    (ii) seeding the medium to be treated with said ferment in an activated form.

14. A process according to claim 13, wherein the contacting of the lactic acid bacteria-based ferment with said activator is conducted within a liquid medium.

15. A process according to claim 14, wherein the liquid medium is water.

16. A process according to claim 13, wherein the process can be implemented with the aid of a seeding device.

17. A process according to claim 16, wherein the seeding device is a sealed tank.

18. A process according to claim 17 wherein the sealed tank is in the form of a disposable tank and/or a tank which is secured to a movable station.

19. A process according to claim 17, wherein the sealed tank is in the form of a pocket equipped with an internal agitation system and intake and outlet means.

20. A process according to claim 13, wherein step (ii) is carried out at a temperature of between 5° C. and 45° C.

21. A process according to claim 13, wherein step (ii) is carried out over a period of time of up to 72 hours.

22. A process according to claim 13, wherein step (ii) is carried out over a period of time of up to 48 hours.

23. A process according to claim 13, wherein step (ii) is carried out over a period of time of up to 24 hours.

* * * * *